United States Patent [19]

Linner et al.

[11] Patent Number: 4,807,442

[45] Date of Patent: Feb. 28, 1989

[54] CRYO-SLAMMING APPARATUS AND METHOD FOR ULTRARAPID COOLING OF BIOLOGICAL SAMPLES

[75] Inventors: John G. Linner; Stephen A. Livesey, both of The Woodlands, Tex.

[73] Assignee: Board of Regents The University of Texas System, Austin, Tex.

[21] Appl. No.: 102,395

[22] Filed: Sep. 29, 1987

Related U.S. Application Data

[63] Continuation-in-part of Ser. No. 939,701, Dec. 3, 1986, Pat. No. 4,707,998.

[51] Int. Cl.$^4$ ............................................. B01D 8/00
[52] U.S. Cl. .................................... 62/55.5; 62/275; 118/50.1
[58] Field of Search ..................... 62/55.5, 514 R, 275, 62/78, 265, 268, 100, 62, 349; 34/92; 118/50, 50.1; 424/3, 4; 422/131

[56] References Cited

Foreign Patent Documents

614,532 11/30/79 Switzerland.

PUBLICATIONS

Polaron Instruments Inc., "The Slammer" (brochure).
Reichert-Jung, "Cryofract 190 Cryoblock" (brochure).
Reichert-Jung, "Cryovacublock"–Instruction Manual.
Escaig, Jacques, "Control of Different Parameters for Optimal Freezing Conditions", *Science of Biological Specimen Preparation*, pp. 117–122.
Handley, Dean A., et al, "The Design and Use of a Simple Device for Rapid Quench–Freezing of Biological Samples", *Journal of Microscopy*, Mar. 1981, at pp. 273–282.
Escaig, Jacques, "New Instruments Which Facilitate Rapid Freezing at 83K and 6K", *Journal of Microscopy*, Jun. 1982, at pp. 221–229.
Boyne, Alan F., "A Gentle, Bounce-Free Assembly for Quick-Freezing Tissues for Electron Microscopy: Application to Isolated Torpedine Ray Electrocyte Stacks", *Journal of Neuroscience Methods*, 1 (1979), pp. 353–364.
Coulter, H. David, "Freezing and Drying of Biological Tissues with a Toggle-Link Helium Freezer and an Improved Freeze-Drying Apparatus: Application to Neuropeptide Immunocytochemistry", Journal of Electron Microscopy Technique, (1986), at pp. 315–328.
Med-Vac Inc., "Cryopress" (brochure).
Quick Freezing Devices, "Quick Freezing by Bounce–Free Delivery" (brochure).
Moor, H. et al, "The Influence of High Pressure Freezing on Mammalian Nerve Tissue", *Cell and Tissue Research*, (1980), at pp. 201–216.

*Primary Examiner*—Henry A. Bennet
*Attorney, Agent, or Firm*—Arnold, White & Durkee

[57] ABSTRACT

A method and apparatus for ultrarapid cooling of tissue samples against a chilled cryogenic surface. The cryogenic surface is enclosed in a high vacuum chamber during cooling of the cryogenic surface. Dry non-condensable room temperature gas is introduced from an external source to raise the chamber pressure just prior to slamming or plunging a sample against the cryogenic surface. The cryogenic surface is heated for regeneration or cleaning purposes between each successive sample.

21 Claims, 5 Drawing Sheets

CRYO-SLAMMING APPARATUS AND METHOD FOR ULTRARAPID COOLING OF BIOLOGICAL SAMPLES

CROSS-REFERENCE TO AND INCORPORATION BY REFERENCE OF RELATED APPLICATION

This application is a continuation-in-part of commonly-assigned, copending U.S. patent application Ser. No. 939,701 filed Dec. 3, 1986 now U.S. Pat. No. 4,707,998. The subject matter of said application Ser. No. 939,701 is hereby incorporated by reference.

BACKGROUND OF THE INVENTION

1. Field of the Invention

This invention relates to cryo-fixation apparatus and method for the ultrarapid cooling of biological samples. Ultrarapid cooling is a preparatory step to the cryo preparation of biological samples in apparatus such as that described in commonly assigned U.S. Pat. Nos. 4,510,169 and 4,567,847 issued to John G. Linner and commonly referred to as "The Linner Process" or "The Linner Apparatus". It is well known in the medical arts that to examine biological samples and determine the cellular structure and function thereof, the samples must be "fixed" with minimal alteration of ultrastructural integrity prior to the application of nearly all analytical methodologies. The apparatus of this invention can be used to ultrarapidly cool biological samples without the formation of resolvable ice crystals so that the ultrastructural integrity of the sample is not altered. In most samples that are more than a few microns in thickness the ice crystals will range in size from amorphous at the leading edge to hexagonal in the interior of the tissue. There is a gradient effect in the formation of ice crystals.

The terms "biological samples", "tissue samples", and "biological tissue" are used throughout this disclosure to refer to samples that can be ultrarapidly cooled by the method and apparatus of this invention. The terms are used interchangeably and are not intended as a limitation on the functional capability of the method or apparatus disclosed herein. The terms should be understood to include small tissue samples appropriate for microscopic examination and larger tissue masses such as corneas which are appropriate for transplantation. The terms should be understood to include any material composed of one or more cells, either individual or in complex with any matrix or in association with any chemical; and to include any biological or organic material and any cellular subportion, product or by-product thereof. The terms should be further understood to include without limitation sperm, eggs, embryos, blood components and other cellular components. The contemplated utility of the apparatus of this invention is not limited to specific types or sizes of tissue, rather it should be understood to refer to any tissue made up from cells. The apparatus of this invention can be designed or adapted to any size, shape or type of cellular tissue. Therefore, the terms "tissue" and "tissue samples" are used interchangeably and are not limiting on the uses to which the method and apparatus of this invention can be placed.

Although the method and apparatus of this invention are preferably used as a preliminary step in the cryopreparation of biological samples for ultrastructural analysis, i.e. electron microscopy, it should be understood that this is not intended as a limitation on the utility of the apparatus and method of this invention. To the contrary, the ultrarapid cooling method and apparatus of this invention have demonstrated utility in any area in which the ultrastructure of cellular components is desirably maintained in an unaltered state. Examples of such utility include, but are not limited to, electron microscopy, tissue preservation, tissue and organ transplants and various analytical and diagnostic methodologies. Therefore, although the method and apparatus of this invention are typically described in relationship to electron microscopy this should be understood not to be a limiting factor on the utility of the invention.

Although the examination of tissue by use of various microscopes or related magnifying apparatus has been practiced for many years, there has been an inherent problem in preparing tissue for use with contemporary high resolution analytical microscopes, such as the STEM electron microscopes, which permit the examination of sample constituents via X-ray analysis at powers of from $500\times$ to $500,000\times$ with point to point resolution of 2 to 3 Angstrom units.

It is difficult to interpret the results of tissue analysis while concomitantly assessing the extent of various artifacts produced during the tissue preparation processes. It is thus essential that artifacts be avoided wherever possible. The term "artifact" refers to a product of artificial character due to extraneous agency. Another problem results from physical shrinkage of the tissue sample itself, which results in alteration of ultrastructure and massive rearrangement of infrastructural resolution.

During the so-called "Golden Age of Morphology" the predominant underlying goal in qualitative and quantitative microscopy has been an aesthetically pleasing image. This goal is readily attainable with the fixation methods and apparatus which are currently available. However, it has become essential that the aesthetically pleasing image, which is produced by the preparation process, also yield a tissue sample which accurately reflects the true condition of tissue in the living organism, i.e., approaching the "living state." This is the problem which is addressed and solved by the Linner =Apparatus and Linner Process TM. One essential step in the preparation process is the cryopreparation or cryofixation procedure (as opposed to the freezing procedure). The cryo-preparation method and apparatus of this invention results in the preparation of tissue samples which are readily usable in known magnification and analytical apparatus.

In currently known cryopreparation and freeze-drying devices and methods, problems and limitations are encountered in attempts to rapidly cool the tissue sample without physically harming the sample. If the temperature decrease in the sample to its full depth does not take place at a sufficiently rapid rate, artifacts appear, the ultrastructural integrity of the sample may be damaged and the sample will not appear in its "living state". The prior art has therefore attempted to achieve a rapid rate of temperature decrease to the full depth of the sample, in order to minimize such damage.

Although the primary thrust of this application is in the preparation of tissue samples for analysis by current magnification apparatus, the invention is not intended to be so limited. More specifically, the "preparation" of tissue should be understood to refer to preparation of tissue for analysis as well as the cryofixation of tissue in anticipation of transplantation, modification, in vitro or in vivo cellular growth, fertilization, animated suspension or the more typical resin impregnation, setting, infiltration and analysis. The apparatus of this invention can be used to prepare tissue for any medical or analytical procedure without the ultrastructural damage previously thought to be inevitable in cryopreparation.

The apparatus of this invention is to be distinguished from contemporary freeze-drying apparatus. Freeze-drying is a technique which is well known in the art together with the equipment necessary to implement such freeze-drying. See, for example, U.S. Pat. No. 4,232,453. Although in certain freeze-drying techniques liquid nitrogen is used as a cooling medium, the tissue or sample itself does not attain such temperature. Freezedrying normally contemplates sample temperatures of $-50°$ C. to $-80°$ C. In contrast, the ultrarapid cooling step of the cryopreparation process of the Linner Process TM and apparatus contemplate sample temperatures of $-196°$ C. or colder. Therefore, for purposes of this application the terms "cryopreparation" and "cryofixation" are used in distinction to conventional "freezing" technology.

Description of the Related Art

The most common prior art method for preparation of tissue samples for analysis is by means of chemical fixation and organic solvent dehydration. Inherent in prior art processes is the concomitant artifact creation, sample shrinkage and resultant damage to and modification of tissue characteristics. These tissue characteristic modifications, whether in the form of artifacts or the like, require interpretation by the individual or apparatus analyzing or evaluating the sample. This introduces, in many instances, an unsatisfactory risk of error.

Chemical fixation is a well known technique and has served the analytical biologist well for many years and undoubtedly will continue to do so in certain limited applications. However, as the use of tissue sample analysis becomes more complex and the use of such analysis becomes more widespread, alternatives to chemical fixation are demanded. This is especially true as advances are being made in the magnification and analytical apparatus which are available. It is necessary that tissue preparation methods and the apparatus necessary to prepare tissue samples be equally advanced as the analytical tools, i.e., electron microscopes, which are being used to analyze the samples. Obviously, if the technology for tissue sample preparation is inferior to the technology of microscopy then the advanced microscopes cannot be used to full advantage by the morphologist or other tissue examiner.

Similarly, it is essential that cryopreparation methods and apparatus develop concurrently with other medical technology, i.e., surgical transplant techniques, bioengineering and biogenetics. In short, cryopreparation is an essential intermediate step in evolving processes using or analyzing cells or tissue. If cryopreparation apparatus does not evolve then the thrust of medical technology into unexplained and unexplored medical arts will be blunted. The apparatus of this invention represents the cryopreparation breakthrough that will permit research into the use and preparation of biological tissue to keep pace with other advances in medical technology. The ultrarapid cooling apparatus of this invention provides the mechanism for eliminating the problems associated with available cryofixation apparatus.

An alternative to chemical fixation and organic solvent dehydration is freeze-drying cryofixed samples. Freeze-drying following cryofixation is a well documented and well known technique for tissue preservation. It has several advantages. Cryofixation results in a near-instantaneous arrest of cellular metabolism. There is also a stabilization and retention of soluble cell constituents through elimination of solvent contact with the sample. These are significant advantages to cryofixation freeze-drying that have resulted in a great deal of research in attempting to apply cryofixation and freeze-drying techniques to known tissue preparation processes.

Unfortunately, freeze-drying technology inherently possesses a number of disadvantages relevant to tissue preparation methodologies. The primary disadvantage in currently available freezing techniques and apparatus is the inherent formation of ice crystals. As can be readily appreciated, the formation of ice crystals destroys the ultrastructural integrity of the tissue sample being reviewed. The image is distorted and the cytoplasm becomes reticulated. The formation of ice crystals in the sample can also result in a change in pH within microcompartments of the tissue (eutectic formation) which possibly can result in abnormal tertiary conformation of macromolecules. There is also the possibility that proteins will denature and precipitate. These are but a few of the disadvantages which are inherent in conventional freezing/freeze-drying processes.

This general topic is discussed in some detail together with other prior art methods in an article entitled "Freezing and Drying of Biological Tissues for Electron Microscopy", Louis Terracio and Karl G. Schwabe, published in *The Journal of Histochemistry and Cytochemistry.* Volume 29, No. 9 at pp. 1021–1028 (1981). Problems associated with artifact formation are described in "Understanding the Artefact Problem in Freeze-Fracture Replication: A Review", *The Royal Microscopical Society,* (1982) at pp. 103–123.

A general principle found applicable to freezing techniques, which has demonstrated utility in the preparation of tissue samples, is that as the cooling rate increases, tissue fluids can be "vitrified" without the separation of water to extracellular spaces. The term "vitrified" or "vitrification" refers to the cryopreparation of tissue samples without the formation of resolvable ice crystals within the cellular structure. It has been postulated that regardless of the rate of cooling, ice crystals may still be formed, but as the cooling rates increase tee size of the intracellular ice crystals decreases. The small size or absence of ice crystals at high freeze rates is of course a substantial advantage in morphology retention as this results in minimal artifact creation and minimal ultrastructural alteration or damage during tissue dehydration. The apparatus of this invention provides the ultrarapid cooling of one or more tissue samples to the vitreous phase in less than one second. The ultrarapid cooling according to the present invention is followed by dehydration of the tissue sample while in the state of reduced partial pressure of water vapor without substantial ultrastructural damage to the tissue cells.

Historically, the criteria by which the techniques for rapid supercooling have been judged was not the cooling rate of the system but simply the temperature of the environment in which the tissue was frozen. Thus, the term rapid supercooling has been applied to any system in which the supercooling agent has a temperature of −150° C. or below. The effectiveness of a cooling system, however, is dependent upon the rate at which heat is removed from the sample. Heat transfer is dependent not only on the temperature of the freezing system but also on its physical and thermal characteristics, as well as the size and thermal characteristics of the tissue.

The most commonly used technique for rapid supercooling is to immerse or "quench" the sample in a fluid cooling bath. The most commonly used fluids for quenching are liquid nitrogen, isopentane, propane and fluorocarbons such as Freon 12 and Freon 22. Although liquid nitrogen is generally regarded as an ideal quenching fluid due to its low temperature (−196° C.), there are inherent disadvantages in the use of liquid nitrogen due to the occurrence of tissue surface film boiling caused at least in part by the low heat of vaporization of liquid nitrogen. Film boiling is a characteristic of liquid nitrogen that inhibits the heat transfer rate by actually insulating the sample.

An alternative method for rapid supercooling is applying the tissue sample to the polished surface of a cryogenically cooled material such as the surface of a chilled metal block. This typically involves opposing the tissue sample to a polished flat metal surface by pressing it firmly against the surface of the metal. Silver and copper are typically used as the polished metal blocks. This method is designed to take advantage of the high thermal conductivities and heat capacities of these metals when cooled to liquid nitrogen or liquid helium temperatures. The critical step in chilling on the surface of a metal is making firm contact with the dry, chilled metal surface with no rotational, translational or rebounding motion. Certain commercially available apparatus having known utility in the medical arts address and provide "bounce-free" freezing. Credit for the development of this apparatus is generally accorded to Dr. Alan Boyne of the University of Maryland School of Medicine.

The Boyne apparatus and method included one or more copper bars partially submerged in a container filled with liquid nitrogen at −196° C. The end of the copper bar was a mirror-finished smooth cryogenic surface, and the thermal conductivity of copper enabled the surface to be cooled. Cold nitrogen gas from vaporization of the liquid nitrogen, which escaped past the end of the copper bar, helped to reduce the contaminants on the cryogenic surface. A tissue sample was then dropped by gravity against the surface. To reduce the bounce of the sample against the surface, the Boyne sample delivery assembly employed a weight dampening system utilizing glycerol to absorb the impact. Each copper bar must be cleaned after slamming a sample. The drawbacks of the Boyne apparatus included problems of hydrocarbon contamination and condensation on the cryogenic surface, inability to eliminate all bounce or vibration between the sample and surface, undesirable precooling of the sample with escaping nitrogen gas, and delays for cleaning and regenerating the cryogenic surface of the copper bars between each sequential sample. The Boyne method and apparatus thus could not reliably provide tissue samples with good ice crystal-free zones nor was it capable of properly vitrifying the samples beyond a depth of 10 to 15 microns.

Further development of freezing tissue samples against a metal block has been credited to Jacques Escaig of Paris, France. The method and apparatus of Escaig is described in "Control of Different Parameters For Optimal Freezing Conditions", Jacques Escaig, published in *Science of Biological Specimen Preparation*, at pp. 117-122 (1984). The Escaig apparatus also is disclosed in Swiss patent No. 614,532, French patent No. 2,337,878 and German patent No. 2,700,196. Escaig provided several significant features not shown in earlier methods or devices for vitrifying tissue against a metal block. The Escaig method and apparatus cool a copper block with liquid helium, rather than liquid nitrogen, in order to increase the cooling rate of a tissue sample or specimen. Escaig disclosed that the average thickness of ice crystal-free zones in the tissue sample were much larger when the copper block was cooled by liquid helium rather than liquid nitrogen. Additionally, Escaig pointed out that the factors influencing the freezing process, independent of the tissue sample itself, are thermal contact between the specimen and metal block, condition of the block surface, specimen slipping, sample holder bounce and sample holder contact strength. Escaig obtained some control of these factors by utilizing a vacuum pump to keep the metal block under vacuum of $1 \times 10^{-3}$ mbar until just before slamming the specimen against the block, in order to reduce contamination on the block surface. Escaig also utilized an electromagnet to bring the specimen in contact with the block in order to improve mechanical contact between the specimen and the block.

According to the Escaig apparatus and method, a copper block is enclosed in a vacuum chamber. The chamber is then evacuated to approximately $1 \times 10^{-3}$ mbar with an external vacuum pump system. After a vacuum is reached in the chamber, Escaig employed an external nonreusable cryogen source—liquid helium pumped from a reservoir—to cool the copper block. The liquid helium is transmitted to a passage adjacent to the block through a conduit in the vacuum chamber. When the block is cooled to the desired temperature, Escaig used an electropneumatic system to open a stem insert in the liquid helium passage for releasing cold helium gas for several seconds into the vacuum chamber itself. The cold helium gas admitted into the vacuum chamber is obtained from vaporization of the liquid helium which was used to cool the metal block. The cold helium gas raises the pressure inside the vacuum chamber. When atmospheric pressure is reached inside the vacuum chamber, a shutter providing access to the vacuum chamber is spring biased to open the chamber and activate downward movement of a sample delivery assembly, which plunges or slams the tissue sample through the shutter opening and against the block. Opening of the shutter also triggers closing of the stem insert to stop the release of cold helium gas into the chamber.

Several problems have been encountered in the Escaig apparatus. Because Escaig used cold helium gas to bring the vacuum chamber up to atmospheric pressure, a tissue sample precools for approximately 15 milliseconds as it descends through a layer of cold helium gas at atmospheric pressure prior to plunging or slamming against the metal block. The precooling effect of the Escaig device is undesirable due to unwanted effects, such as ice crystal formation, on the physiology of the tissue sample. Additionally, movement of liquid helium and helium gas through the vacuum chamber inevitably resulted in vibration of the metal block, which was undesirable because it reduced or prevented good mechanical contact between the specimen and block.

Escaig's use of nonreusable liquid helium to cool the block further has proved to be expensive, somewhat unsafe and cumbersome due to the necessity of recooling the entire liquid helium system between each tissue sample. The end result was extremely slow turnover time for regenerating the copper block between each sample. Additionally, cleaning the block in the Escaig apparatus proved difficult because of condensation on the block forming after a sample was slammed against the block. To remove the condensation, pressurized nitrogen gas and hot air could be applied against the block. However, removal of the block for repolishing or other cleaning required disassembly of the vacuum chamber itself. Even if the block was not removed, the problems in regenerating the block surface resulted in turnover time between samples which is commercially unacceptable. It was therefore not possible to use the Escaig device if a large number of sequential samples was desired.

The cryopreparation apparatus and method according to the present invention solves the problems inherent in the prior art including the Escaig apparatus and method. The present invention addresses the problems in the prior art of slow turnover time between the vitrification of tissue samples, by enabling several samples to be vitrified sequentially. The present invention also solves the problems in the prior art caused by undesirable precooling of the tissue sample before contact with the cryogenic surface, cleaning and reheating the cryogenic surface between each sample, and removal of the cryogenic surface from the apparatus.

SUMMARY OF THE INVENTION

The apparatus and method of the present invention provide for ultrarapid cooling or vitrification of tissue samples by slamming or plunging the samples against a chilled cryogenic surface. The apparatus contemplates chilling of the tissue sample against a mirror-finished smooth cryogenic surface. The cryogenic surface is enclosed in a ultra vacuum chamber. Under certain circumstances an ultra-high hydrocarbon free vacuum chamber may be used. For purposes of this application the terms "ultra-high vacuum" and "high vacuum" are used interchangeably although it is recognized that there are technical distinctions.

In the preferred embodiment, the shutter opening to the vacuum chamber and the movement of the tissue sample on the plunger are pneumatically controlled in order to assure precise timing of the shutter and plunger, with a constant rate of descent. Noncondensable dry helium gas at room temperature is introduced into the chamber just prior to pneumatically activating the shutter and plunging the sample against the block. The introduction of helium gas enables the chamber pressure to be raised and the shutter to be opened without undesirable condensation on the cryogenic surface, or dehydration and precooling of the tissue sample during its downward movement through the shutter opening towards the cryogenic surface. An external dry helium source is used to supply dry helium to the chamber.

In the preferred embodiment, the cryogenic surface may be regenerated rapidly between slamming of successive samples. The rapid regeneration is enabled by the use of a heating unit associated with the cryogenic surface. The heating unit is activated between samples to heat the cryogenic surface for cleaning and removing condensation.

Before a sample is slammed against the cryogenic surface, a hydrocarbon-free vacuum must be obtained in the vacuum chamber surrounding the cryogenic surface. The cryogenic surface is then cooled with a liquid nitrogen or liquid helium system which circulates liquid nitrogen or helium through a cooling chamber. The cooling chamber, which is enclosed within the vacuum chamber, holds the cryogenic block. The end of the cryogenic block is a cryogenic surface which extends from the top of the cooling chamber and is sealed in relation thereto. Dry helium gas is then introduced into the vacuum chamber to bring the pressure to atmospheric before the slamming operation takes place. The present invention enables sequential vitrification of tissue samples against the cryogenic surface without substantial delays for regeneration inherent in the prior art and facilitate rapid recooling.

Another advantage of the apparatus of this invention is the ability to cryoprepare tissue without overt disruption or destruction of the morphological characteristics of the ultrastructure of tissue cells. The cryo-slamming method and apparatus of the present invention provide for ultrarapid cooling of tissue samples so that the tissue may be dehydrated while maintained in the solid, vitreous phase without creating unnecessary artifacts which restrict interpretation by conventional analytical apparatus.

The cryo-slamming apparatus and method of the present invention may demonstrate an extraordinary application in the transplanting of corneal tissue. Prior to this invention attempts to transplant corneas which involved a necessary freezing or freeze-drying of the cornea after removal from the donor invariably resulted in a clouded cornea upon transplanting. The clouding remained for from as little as several days to the life of the transplanted cornea. This physical condition of the transplanted cornea was caused by ice crystal formation in the cornea itself and concomitant damage to the stroma. Use of the apparatus of this invention has enabled ophthalmologists to cryoprepare corneas and to then transplant those corneas to recipients with virtually negligible clouding or crystal formation. The ability to so transplant corneas represents an exceptional advantage to the process of this invention as well as a medical breakthrough in corneal transplant surgery.

DETAILED DESCRIPTION OF THE PREFERRED EMBODIMENT

In the apparatus of this invention it is a fundamental prerequisite that the desired tissue is obtained. Tissue samples are collected by a variety of means, i.e., surgical extraction, withdrawn blood samples, binders and any of a variety of other techniques which are well known and conventional. The particular method of obtaining the biological sample is not limiting on the apparatus of this invention. However, the preparation of the tissue sample in the apparatus of this invention is enhanced if the tissue sample is processed as soon after exercising as is possible.

The preparation of the tissue sample takes place immediately as it is received. The tissue sample cannot be retained in a fixative, i.e., formaldehyde, or another biologically active stabilizing solution, in an attempt to maintain the sample during shipping, storage or other necessary operations. It is also critical that the sample not be routinely frozen or otherwise physically modified prior to preparation according to the method of this invention. The sample may later be physically sectioned or otherwise physically prepared for long-term storage in apparatus or use with various currently available commercial analytical apparatus.

In one application of this invention a tissue sample is prepared for analysis. The preferred optimum biological sample for preparation in the apparatus of this invention is a fresh one cubic millimeter biopsy sample. This sample must be vitrified as soon as possible. By vitrifying or vitrification it is intended to make reference to a process which results in cryofixation of the sample which is different from "frozen." In the process of vitrifying, the cooling apparatus which is used renders a portion of the sample in the vitreous phase such that soluble and insoluble moieties contained in the tissue sample are not disturbed, translated, or altered nor are they concentrated (as eutetics). By definition, a vitrified liquid will shatter when undergoing a shear stress, e.g., window glass. The vitreous phase involves the conversion of liquid water into an amorphous or "glass" phase. This is accomplished by rapidly supercooling the tissue sample by opposing it "bounce-free" onto the highly polished (mirror-like) contaminate-free cryogenic surface preferably at between $-265°$ C. and $-196°$ C. It is preferred that such rapid supercooling be completed in less than one second.

Depending on the anticipated time lag between supercooling of the sample and dehydration of the sample, the sample may be stored submerged in a liquid nitrogen dewar at $-196°$ C. Once the sample has been dried and embedded properly it may be stored virtually indefinitely without cytoplasmic reticulation or other forms of cellular catabolism which will cause modifications and crystal lattice transitions resulting in undesirable artifacts which render the tissue uninterpretable as analytical data.

Figure 8:
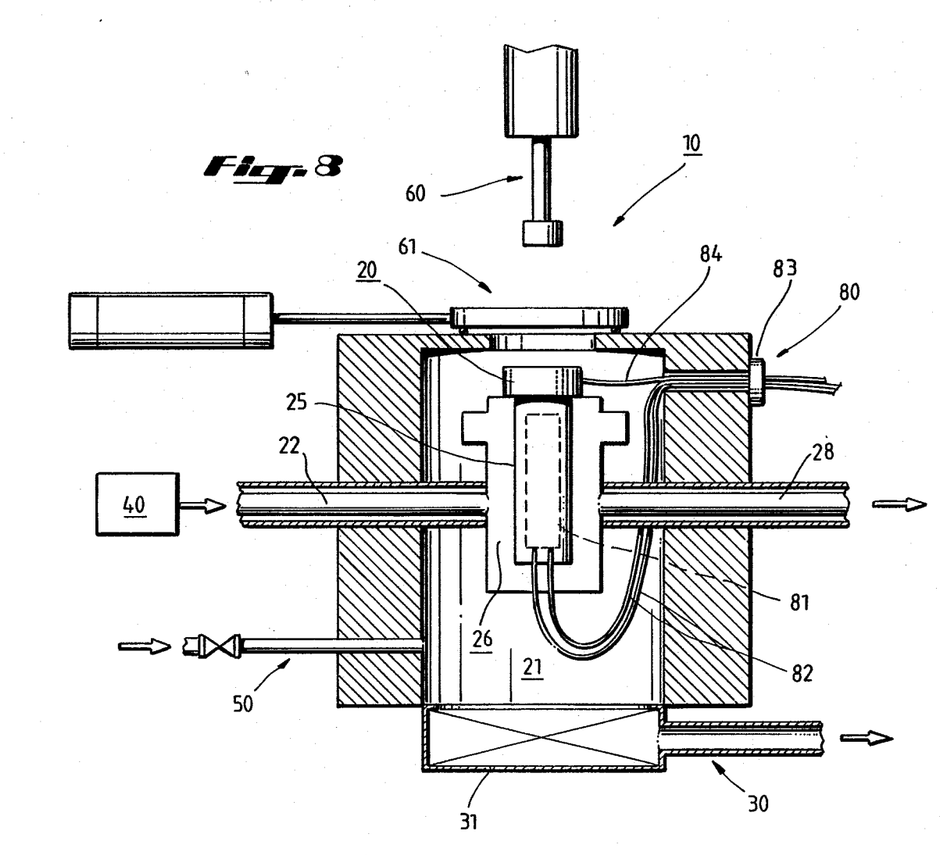
FIG. 8 is a schematic drawing of the components of this invention demonstrating the functional relationship of the elements.

As shown schematically in FIG. 8, the apparatus for ultrarapid cooling of this invention 10 includes a cryogenic surface 20 and a vacuum system 30 for imparting a vacuum to the atmosphere surrounding cryogenic surface 20. The apparatus further includes cooling means 40 which function to bring the cryogenic surface 20 to cryogenic temperatures. Vacuum reversal means 50 are also associated with the atmosphere surrounding cryogenic surface 20. A sample delivery assembly 60 and a shutter assembly 61 are functionally associated with the cryogenic surface 20 and include means for mounting biological tissue and means for transferring the biological tissue from outside of the chamber enclosing the cryogenic surface to inside the chamber and into contact with cryogenic surface 20. Temperature control means 80 are functionally associated with the cryogenic surface 20 to control the temperature of cryogenic surface 20.

Figure 1:
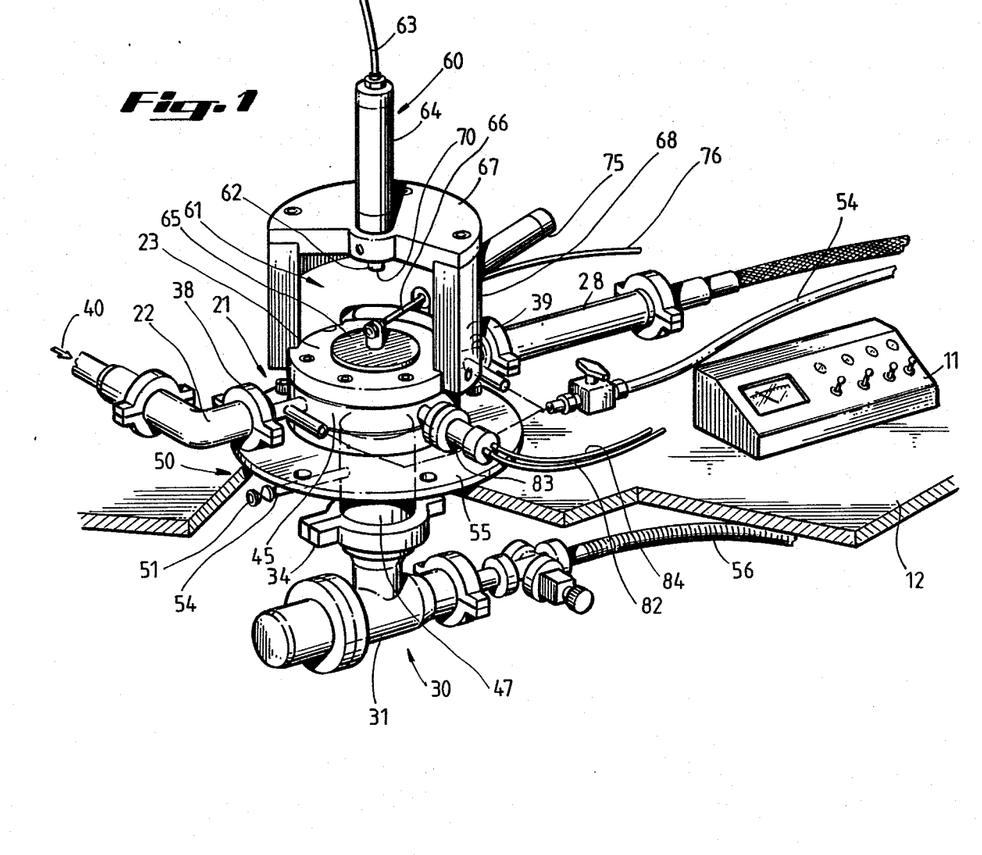
FIG. 1 is a perspective view of the preferred embodiment of the cryo-slamming apparatus according to the present invention.
Figure 4:
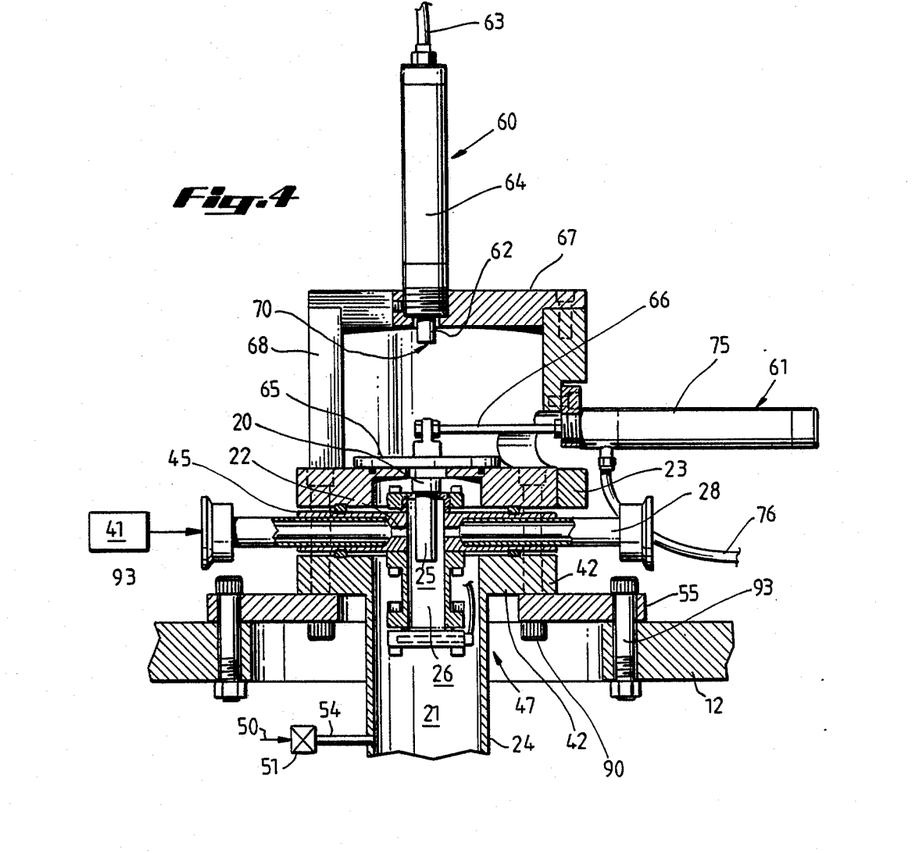
FIG. 4 is a cross-sectional view of the vacuum chamber and delivery assembly according to a preferred embodiment of the present invention, taken along section line 4—4 of FIG. 3.

FIG. 1 is a perspective view of the preferred embodiment of the present invention. In the preferred embodiment, major components of cryopreparation apparatus 10 include sample delivery assembly 60, vacuum chamber 21, vacuum means 30, and controls 11. The cryopreparation apparatus is mounted on mounting flange 55 which is fixed to horizontal surface 12. The sample delivery assembly 60 comprises a plunger 62 which is slideably mounted in plunger housing 64. At the end of the plunger is a sample holder 70 (FIG. 4). Pneumatic conduit 63 is connected to the plunger housing 64. The plunger 62 is pneumatically actuated to move the tissue sample downward against the cryogenic surface 20 when shutter 65 is pneumatically opened.

The sample delivery assembly 60 is mounted on base plate 67 which is supported over the vacuum chamber 21 by means of a circular sidewall 68. The sample delivery assembly is cooperatively aligned with the vacuum chamber 21 so that it may be actuated pneumatically to move the tissue sample downward against a cryogenic surface 20 when the shutter assembly 61 opens access to the vacuum chamber 21.

The shutter assembly 61 comprises a shutter 65, which is mounted on rod 66 extending from rod housing 75. The shutter assembly 61 is pneumatically actuated. Pneumatic conduit 76 extends to the rod housing 75. The shutter 65 seals the vacuum chamber end plate 23, and moves the shutter to open the vacuum chamber when a sample is to be slammed against the cryogenic surface. The shutter 65 is actuated pneumatically and is movable to open cooperatively with downward movement of plunger 62. The pneumatic actuation provides continuous force at a constant rate of descent to the plunger 62, with a functionally effective delay between the time shutter 65 is open until sample application against the cryogenic surface 20. In most instances the delay will be less than 5 milliseconds.

The vacuum chamber 21 includes upper end plate 23, conduit housing 45, and vacuum chamber housing 47. These components are mounted together in sealing relationship and are preferably composed of stainless steel and constructed so they may be vacuum sealed. A cryogenic surface 20 is located within the vacuum chamber 21. Cooling means 40 is provided to cool the cryogenic surface 20 via cooling inlet conduit 22 which is connected by cooling inlet coupling 38 to the conduit housing flange 45, which in the preferred embodiment is a two-sided conflat flange. Further, cooling outlet conduit 28 is connected by cooling outlet coupling 39 to an opposing side of the conduit housing 45. The inlet 22 and outlet 28 are used to circulate cooling fluids such as liquid nitrogen or helium to cool the cryogenic surface prior to slamming a tissue sample against that surface.

The vacuum means 30 is connected to the lower end of vacuum chamber housing 47 with a vacuum coupling 34. The vacuum means 30 further includes vacuum valves 31 and vacuum conduit 56. Vacuum means 30 imparts a high hydrocarbon free vacuum to the vacuum chamber 21.

Vacuum reversal means 50 includes vacuum reversal conduit 54 which is connected to vacuum chamber housing 47. The vacuum reversal means 50 also includes vacuum reversal valve 51 to control vacuum reversal flow which, in the preferred embodiment, is dry helium or dry nitrogen gas at room temperature.

The temperature regulator or thermocouple 83 is also connected to conduit housing 45 to regulate the temperature of the cryogenic surface 20 and to regenerate that surface. An electrical connector 82 for the heater and an electrical connector for the thermocouple 84 extend from the conduit housing 45.

Figure 2:
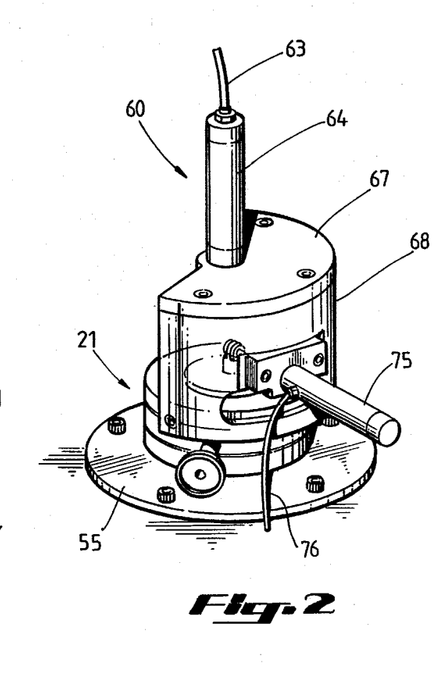
FIG. 2 is a perspective view of the vacuum chamber and delivery assembly according to a preferred embodiment of the present invention.

FIG. 2 shows a perspective view of a preferred embodiment of the vacuum chamber and delivery assembly. According to a preferred embodiment of the present invention, the vacuum chamber 21 is shown with the sample delivery assembly 60 cooperatively mounted above the chamber. As shown, sample delivery assembly 60 includes pneumatic conduit 63 and plunger housing 64. Plunger housing 64 is mounted on base plate 67 and circular sidewall 68 above the sample chamber 21. Also shown in FIG. 2 is rod housing 75 mounted into the side of circular sidewall 68. Pneumatic conduit 76 is connected to the rod housing 75, along with pneumatic conduit 76 to provide pneumatic force to the rod connected to the shutter opening the vacuum chamber 21. Also shown in FIG. 2 is mounting flange 55 which is mounted on the horizontal surface 12.

Figure 3:
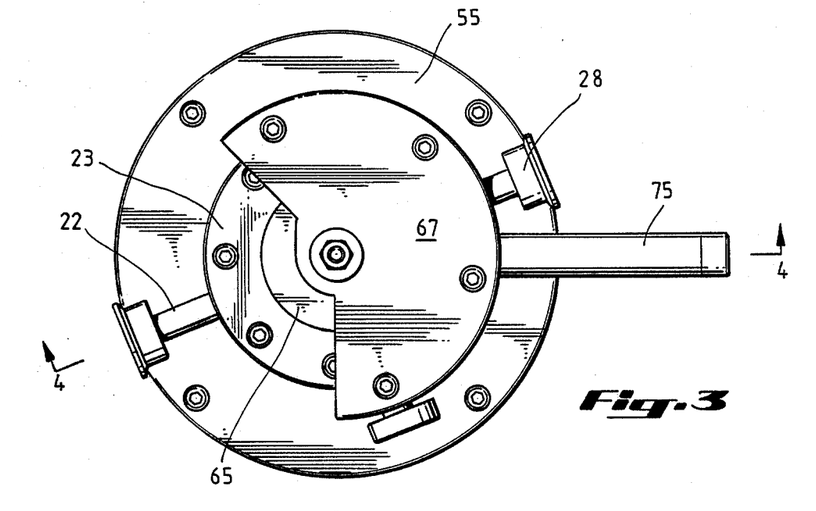
FIG. 3 is a top view of the vacuum chamber according to a preferred embodiment of the present invention.

In FIG. 3, a top view of the vacuum chamber according to the preferred embodiment of the present invention is shown. In the top view, base plate 67 can be seen mounted above the upper end plate 23 of the vacuum chamber. Also shown in FIG. 3 is a mounting flange 55 and rod housing 75. Shutter 65 seals the top of the vacuum chamber upper end plate 23. Additionally FIG. 3 shows the cooling inlet conduit 22 and the cooling outlet conduit 28 for cooling the cryogenic surface mounted within the vacuum chamber 21.

FIG. 4 is a cross sectional view of the vacuum chamber and delivery assembly according to a preferred embodiment of the present invention. FIG. 4 is taken along section line 4—4 of FIG. 3. As shown, sample delivery assembly 60 includes plunger housing 64, plunger 62 extending from the plunger housing and terminating at sample holder 70. The sample delivery assembly also includes pneumatic conduit 63. The sample delivery assembly is mounted on base plate 67 extending from the top of the circular sidewall 68 which is mounted on upper end plate 23 of the vacuum chamber 21. Vacuum chamber 21 comprises upper end plate 23, conduit housing 45 and vacuum chamber housing 47. These components are sealed together in sealing engagement with vacuum chamber screws 90. Shutter 65 seals the opening of upper end plate 23 and is connected to rod 66 extending from rod housing 75. The shutter assembly 61 comprises shutter 65, rod 66, rod housing 75 and pneumatic conduit 76. The rod housing 75 is mounted on circular sidewall 68, and is pneumatically actuated to move the shutter to open the vacuum chamber 21.

Cooling means 40 (see FIG. 8) comprises cryogenic source 41 which supplies cryogenic cooling fluid to inlet conduit 22, through cooling chamber 26 and out the outlet conduit 28. Cooling chamber 26 is mounted within the vacuum chamber 21. The cooling chamber 26 holds the lower region 25 of cryogenic surface 20.

The lower region 25 of the cryogenic surface 20 extends into the cooling chamber which is supplied with fluid such as liquid nitrogen or helium during the cooling process. Vacuum jacket 58 thermally isolates cryogenic effects of the liquid coolant from all but the cryogenic components of the apparatus, i.e., the cryogenic block.

The cryogenic surface 20 may be composed of copper, chromium, gold, silver, diamond or sapphire or combinations thereof or other suitable means having high heat conductivity at low temperatures and providing a mirror finished flat smooth surface for contact with tissue samples. Preferred cryogenic surfaces include copper with a sapphire outer portion or copper with a diamond outer portion. In the preferred embodiment, the lower section 25 of cryogenic surface 20 is maintained within cooling chamber 26.

Still referring to FIG. 4, the vacuum chamber housing 47 comprises vacuum chamber housing flange 42, and vacuum chamber housing sidewall 24. Vacuum reversal means 50 further is mounted to supply a dry helium or nitrogen gas to the vacuum chamber 21. Vacuum reversal means 50 includes vacuum reversal valve 51 and vacuum reversal conduit 54. The vacuum chamber housing flange 42 is mounted on mounting flange 55 and affixed by mounting flange screw 93 on the horizontal surface 12.

Figure 5:
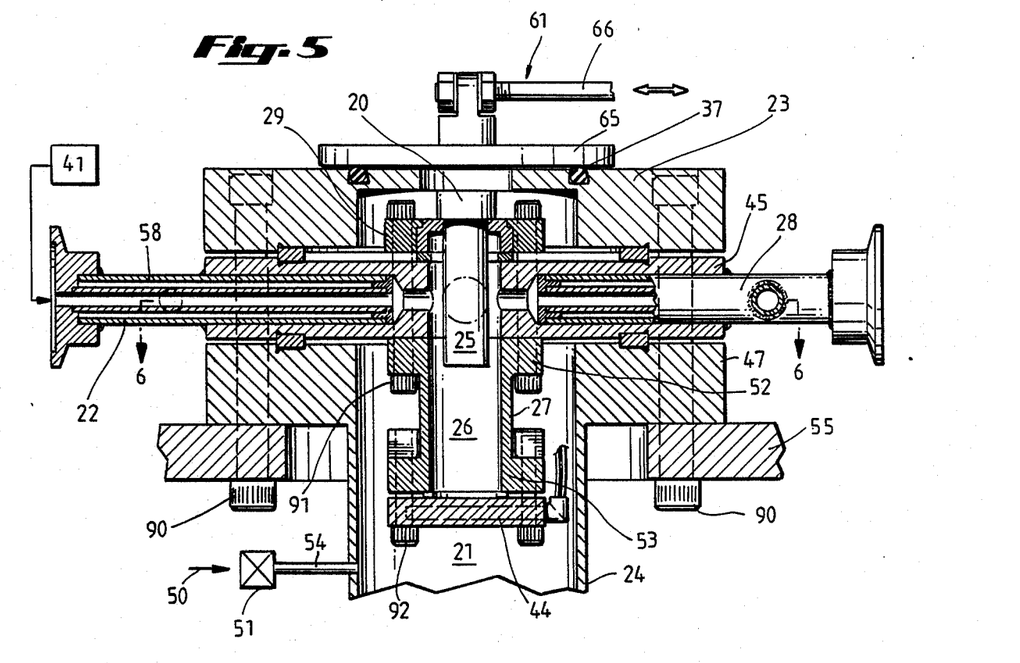
FIG. 5 is a cross-sectional view of the vacuum chamber according to a preferred embodiment of the present invention.

FIG. 5 shows the vacuum chamber and cooling chamber in more detail. As shown in FIG. 5, shutter 65 seals the top of upper end plate. The shutter is opened when the rod 66 is pneumatically actuated to move the shutter out of sealing relationship with the upper end plate. An o-ring 37 is included in the upper end plate 23 for sealing with the shutter 65. The cryogenic surface 20 is shown in FIG. 5 having a lower region 25 maintained within the cooling chamber 26. The cooling chamber 26 further includes cooling chamber upper end plate 29, cooling chamber body 27 and cooling chamber lower end plate 44. Cooling chamber body 27 is sealed to the lower side of conduit housing 45, while cooling chamber upper end plate 29 is sealed to the top of the conduit housing 45. Upper cooling chamber screw 91 connects the cooling chamber, conduit housing 45, and cooling chamber body 27. Cooling chamber body 27 further includes cooling chamber body upper flange 52 and lower flange 53. The lower flange 53 is connected to cooling chamber lower end plate 44 with lower cooling chamber screw 92. Cooling chamber 26 is sealed to hold the cooling fluid such as liquid nitrogen or helium which is circulated through the cooling chamber. This is the only known slamming device that can withstand 20 p.s.i. of coolant pressure for rapid cooling of the cryogenic surface, most prior art devices are effective at no more than 2-5 p.s.i.

Also shown in FIG. 5, cryogenic source 41 supplies cryogenic fluid through cooling inlet conduit 22 which introduces the fluid into the cooling chamber 26 and out the cooling outlet conduit 28. Conduits 22 and 25 are surrounded by vacuum jacket 58. Also shown in FIG. 5 is vacuum chamber housing 47 which is mounted on mounting flange 55 with vacuum chamber screws 90. Vacuum reversal means 50 supplies noncondensable room temperature gas such as dry helium or nitrogen through vacuum reversal conduit 54, controlled by valve 51, which provide access through vacuum chamber housing sidewall 24.

Figure 6:
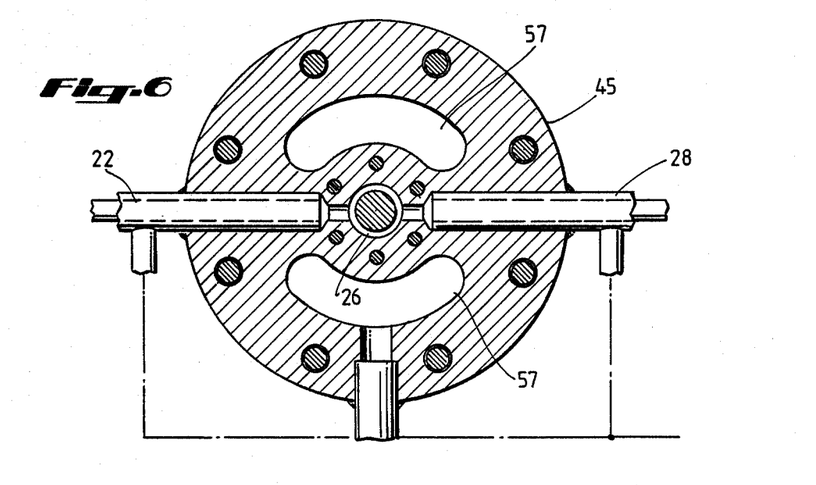
FIG. 6 is a cross-sectional view of the conduit housing according to a preferred embodiment of the present invention, taken along section line 6—6 of FIG. 5.

Now turning to FIG. 6, a cross sectional view of the conduit housing according to a preferred embodiment of the present invention is shown, taken along section line 6—6 of FIG. 5. As shown in FIG. 6, conduit housing 45 includes cooling inlet conduit 22 and cooling outlet conduit 28. The inlet conduit and outlet conduit are surrounded by vacuum conduit 58. Also shown in FIG. 6 is conduit housing orifice 57 which is a portion of the vacuum chamber 21. Thus, the vacuum chamber 21 extends both below and above the conduit housing 45.

Figure 7:
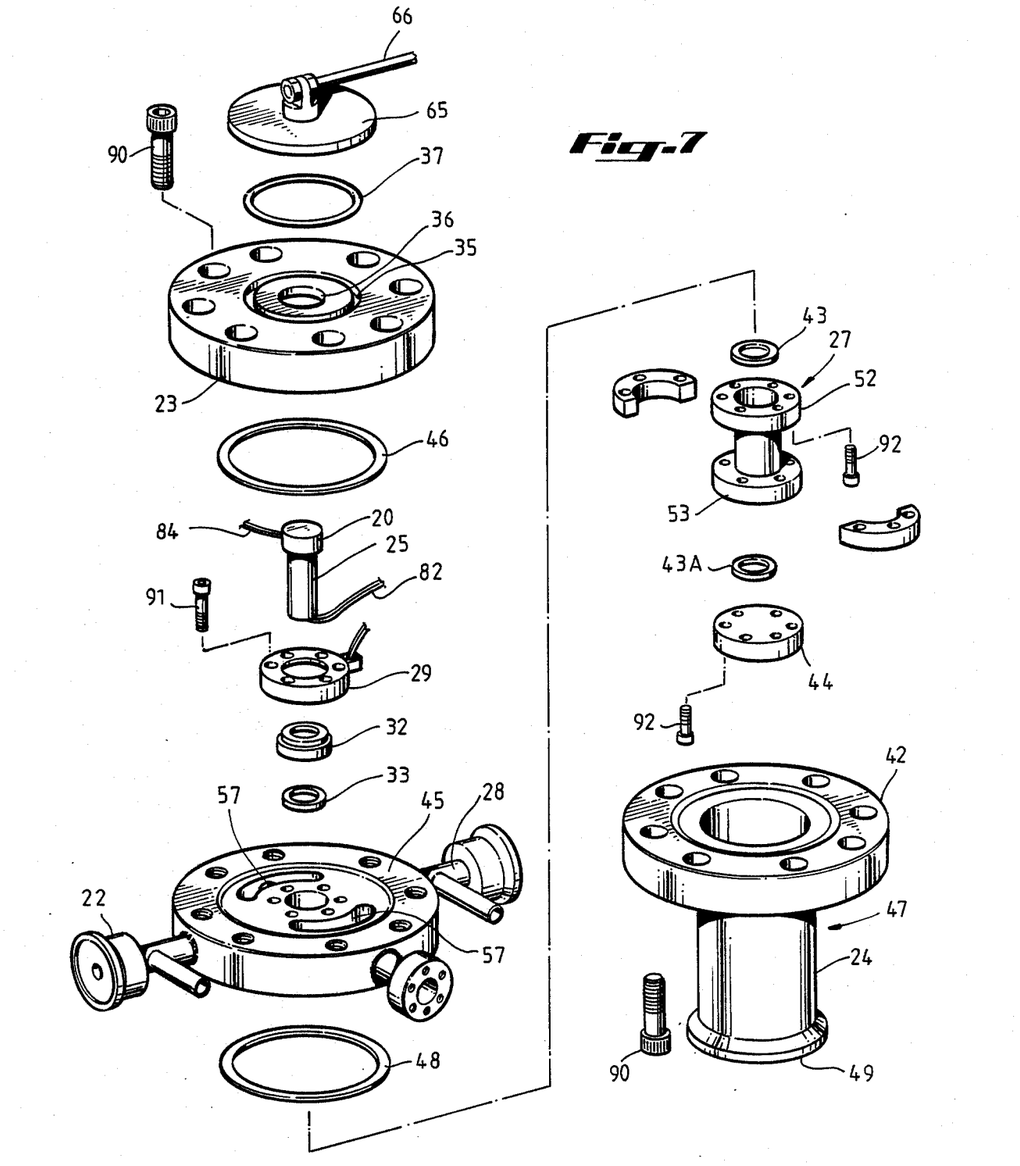
FIG. 7 is an exploded perspective view of the vacuum chamber according to a preferred embodiment of the present invention.

FIG. 7 is an exploded perspective view of the vacuum chamber according to a preferred embodiment of the present invention. As shown in FIG. 7, shutter 65 is removeably connected to rod 66, which seals off the aperture 36 in the vacuum chamber upper end plate 23. A seal or o-ring 37 is provided within concentric groove 35 in the vacuum chamber upper end plate 23. The upper end plate 23 comprises the top portion of vacuum chamber 21. Due to the extreme temperature and pressure conditions, the o-ring 37 may be manufactured of special materials to assure a seal. A conflat flange copper gasket 46 is used to seal the vacuum chamber upper end plate 23 against the conduit housing 45. The cryogenic surface 20 includes a lower section 25 which is maintained within cooling chamber 26. An electrical connector 82 for the heater extends from the lower section 25 of the cryogenic surface. An electrical connector 84 for the thermocouple extends from the cryogenic surface. The lower end 25 of the cryogenic surface includes temperature control means 80 (FIG. 8), which in the preferred embodiment is heating element or cartridge heater 81. The heating element of cartridge heater 81 is shown in FIG. 8.

The heating element or cartridge heater 81 is connected to electrical connector 82, preferably having a temperature regulator. Heating element or cartridge heater 81 thus enables automatic regeneration of the cryogenic surface 20 for rapid turnover of samples. The heating element or cartridge 81 may be used to controllably raise the temperature of the cryogenic surface 20, depending upon the temperature desired for slamming the particular tissue sample. Heating element or cartridge heater 81 is mounted in the lower end 25 of cryogenic surface 20 by conventional fastening means. Heating element 81 is electrically connected to energy means, not shown, by electrical connector 82. Temperature sensing means 83 are electrically connected to cryogenic surface 20 by electrical connector 84.

The cooling chamber 26 is enclosed within the vacuum chamber 21. The cooling chamber 26 comprises cooling chamber upper end plate 29, annular cooling chamber seal 32, and a copper gasket 33 for sealing the upper end plate with the upper surface of conduit housing 45. The lower section 25 of the cryogenic surface 20 is slideably mounted within the cooling chamber upper end plate and bonded with the annular cooling chamber seal 32. Thus, the cooling chamber 26 is sealed from the vacuum chamber 21 while the cryogenic surface 20 extends from the top of the cooling chamber 26. Also shown are conduit housing 45 having conduit housing orifice 57 extending therethrough, along with the fittings necessary to receive cooling inlet conduit 22 and cooling outlet conduit 28, which circulates the cooling fluid through the cooling chamber 26. The conduit housing orifices 57 are part of the vacuum chamber 21. Conflat flange copper gasket 48 is provided to seal the conduit housing 45 with the vacuum chamber flange 42 of the vacuum chamber housing 47. The vacuum chamber housing 47 further includes vacuum chamber housing sidewall 24 and bottom surface of housing 49.

Now referring to the cooling chamber 26, copper gasket 43 seals the cooling chamber body upper flange 52 with the conduit housing 45. Copper gasket 43A seals the cooling chamber body lower flange 53 to the cooling chamber lower end plate 44. Thus, the cooling chamber is tightly sealed within the vacuum chamber 21. Upper cooling chamber screw 91 and lower cooling chamber screw 92 are provided to assemble the cooling chamber with the conduit housing 45. Vacuum chamber screws 90 further are provided to assemble the vacuum chamber upper end plate 23, conduit housing 45 and vacuum chamber housing 47.

An external vacuum pump is utilized to create a vacuum in vacuum chamber 21. The vacuum pump, not shown, preferably is a vibration isolated cryosorption pump and vane pump or equivalent device for creating a vacuum of at least $10^{-4}$ mbar in the chamber 21. The vacuum pump employed can be any of a variety of commercially available pumping apparatus. The vacuum means 30 are identified schematically in FIG. 8.

The cooling chamber 26 is provided with inlet conduit 22 for conveying cooling fluids from a reservoir to vacuum chamber 21. Additionally, the cooling chamber is provided with outlet conduit 28 for purging the chamber 26 of cooling fluid. An external source of coolant with controls is used to regulate the supply of coolant to chamber 26. Cooling materials may be used including liquid nitrogen and liquid helium. One advantage of the apparatus and method of the invention is the ability to supply cooling fluids at substantially increased pressures than prior art devices. Cooling fluids are typically supplied at a pressure from about 10-25 psi, preferably of at a pressure of 15-20 psi and most preferably at 20 psi.

The operation of the present invention in the preferred embodiment is set forth below. Initially, the shutter 65 enclosing the vacuum chamber 21 is closed. The vacuum means is actuated to secure a high vacuum in the vacuum chamber 21. Once a vacuum has been reached in the vacuum chamber 21, cooling fluid is introduced to the cooling chamber through cooling inlet conduit 22 and out the cooling outlet 28. The cooling means 40 is used to cool the cryogenic surface 20 to a temperature of preferably $-185°$ C. or below. The particular temperature for the cryogenic surface may be varied according to the present invention. The temperature desired depends amongst other things the composition of the cryogenic surface and the tissue sample. Temperature control means 80 is used to sense the temperature of the cryogenic surface during the cooling process.

When the desired temperature is reached the vacuum system is isolated and vacuum reversal means 50 is actuated to reverse the vacuum within the vacuum chamber 21. In a preferred embodiment, dry helium gas is used to reverse the vacuum. Alternatively, dry nitrogen gas at room temperature may be used. Vacuum reversal means 50 is used to allow dry helium gas or dry nitrogen gas at room temperature to enter the vacuum chamber 21 and raise the pressure inside the chamber to atmospheric pressure. The use of noncondensable dry helium gas or dry nitrogen gas at room temperature prevents precooling of the tissue sample during movement towards cryogenic surface 20. It should be understood that any other noncondensable gas may be used, preferably at room temperature, to raise the pressure inside the vacuum chamber without undesirable condensation on the cryogenic surface or precooling of the tissue sample. When the vacuum chamber 21 reaches atmospheric pressure, wherein the pressure inside of the shutter 65 equals the outside of the shutter, the shutter 65 is pneumatically actuated to open the access to the vacuum chamber 21. Pneumatic actuation provides a constant rate of descent of the plunger means through the opening in the vacuum chamber upper end plate and against the cryogenic surface 20. The cooling means 40 and vacuum means 30 are turned off during the slamming of the tissue sample against the cryogenic surface, so that the cooling fluid will not impart any undesired vibration to the cooling surface during the slamming process.

Preferably there is a functionally effective delay between the opening of the chamber via the pneumatic shutter and the slamming of the tissue sample against the cryogenic surface. At the time of application of the sample, the cryogenic surface preferably is a temperature of −265° C. to −185° C., depending upon the particular cooling means employed.

After the sample is plunged or slammed against the cryogenic surface 20, cooling means 40 may be reactuated. After slamming, the tissue sample may remain in contact with the cryogenic surface for a desired period of time. Optionally at this point the tissue sample may be removed from the cryogenic surface and placed in a liquid nitrogen dewar for storage and maintained at a cool temperature after it is removed from the sample holder. The pneumatic shutter is then closed against the upper end plate 23. The heating element 81 is then activated to raise the temperature of the cryogenic surface 20. It is preferred that the shutter 65 be closed and a vacuum drawn during heating of the surface to reduce the amount of condensation and/or contaminants deposited on the cryogenic surface 20. The heating step is accomplished under vacuum conditions to allow sublimation without contamination. When the cryogenic surface 20 reaches the desired temperature, preferably room temperature, the cryogenic surface 20 may be cleaned. During the regeneration of the cryogenic surface, the cooling means is shut off so that the desired temperature may be reached.

Now referring to the vacuum reversal means, the vacuum reversal means is actuated only to raise the pressure inside the vacuum chamber 21 to atmosphereic pressure prior to slamming the sample against the cryogenic surface 20. The vacuum reversal means is deactivated as soon as atmospheric pressure is reached. Optionally, after the sample is slammed against the cryogenic surface 20 and removed from the cryogenic surface 20, vacuum means 30 is re-actuated to obtain a vacuum in the vacuum chamber 21 during regeneration of the cryogenic surface.

In the past, the turnaround time between each sequential tissue sample has been slow, due to the time for heating the block and reactivating the entire cooling system. In the present invention the turnaround regeneration time is reduced to between 3–5 minutes or less.

According to the present invention it is possible to vitrify a large number of tissue samples sequentially after regenerating the cryogenic surface between each sample. The cryogenic surface is heated to preferably room temperature, cleaned and rapidly recooled between each tissue sample. During cooling, the cryogenic surface is in a high hydrocarbon free vacuum. The condensation on the cryogenic surface and/or contamination of the cryogenic surface does not occur prior to application of the tissue sample. Precooling of the sample and condensation on the cryogenic surface is prevented by introducing room temperature dry helium gas, dry nitrogen gas, or other non-condensable gas at room temperature, into the vacuum chamber. The present invention also eliminates problems of vibration to the cryogenic surface due to movement of cooling fluid or liquid helium and helium gas proximate to the surface before slamming. The pneumatic shutter and sample delivery assembly also eliminate problems of timing between opening of the shutter and slamming the tissue sample against the cryogenic surface.

Although the preferred embodiment of this invention has been described hereinabove in some detail, it should be appreciated that a variety of embodiments will be readily available to a person designing such cryopreparation apparatus for a specific end use. The description of the apparatus of this invention is not intended to be limiting on this invention, but is merely illustrative of the preferred embodiment of this invention. Other apparatus and components which incorporate modifications or changes to that which has been described herein are equally included within this application.

What is claimed is:

1. Apparatus for the ultrarapid cooling of biological tissue comprising:
    (a) a cryogenic surface adapted to receive biological tissue and to ultrarapidly cool said biological tissue, said cryogenic surface being enclosed within a chamber;
    (b) vacuum means functionally attached to said chamber and adapted to reduce the pressure of the atmosphere surrounding said cryogenic surface;
    (c) cooling means functionally associated with said cryogenic surface and said chamber;
    (d) vacuum reversal means functionally associated with said chamber to increase the pressure of the atmosphere surrounding said cryogenic surface;
    (e) a sample delivery assembly functionally associated with said cryogenic surface and said chamber, said assembly including means for mounting said biological tissue and means adapted to transfer said biological tissue from outside said chamber to said cryogenic surface inside said chamber; and
    (f) heating means functionally associated with said cryogenic surface said heating means being effective to permit rapid regeneration of said cryogenic surface.

2. The apparatus of claim 1 wherein said cryogenic surface is made from material selected from the group consisting of: copper, chromium, gold, silver, sapphire, diamond or combinations thereof.

3. The apparatus of claim 1 wherein said cryogenic surface comprises a major portion of gold, a minor portion of silver, and is copper plated.

4. The apparatus of claim 1 wherein said cryogenic surface comprises a major part of copper and a minor part of sapphire.

5. The apparatus of claim 2 wherein said biological tissue comprises one or more biological tissue samples.

6. The apparatus of claim 1 wherein said ultrarapid cooling is to a temperature of minus 140 degrees C. or below.

7. The apparatus of claim 1 wherein said vacuum means create a vacuum of from about $1 \times 10^{-4}$ mbar to $1 \times 10^{-10}$ mbar.

8. The apparatus of claim 1 wherein said vacuum means comprise a mechanical pump.

9. The apparatus of claim 1 wherein said vacuum means comprise a mechanical pump connected to a high vacuum pump.

10. The apparatus of claim 1 wherein said vacuum means comprise a cryosorption pump.

11. The apparatus of claim 1 further comprising a hydrocarbon trap functionally associated with said vacuum means.

12. The apparatus of claim 11 wherein said hydrocarbon trap comprises a molecular sieve trap.

13. The apparatus of claim 10 wherein said cryosorption pump is encased in a bakeout jacket.

14. The apparatus of claim 1 wherein said cooling means comprise an inlet and an outlet from said chamber, said inlet being connected to a source of cooling fluid, said cooling fluid being selected from the group consisting of liquid nitrogen, helium or combinations thereof.

15. The apparatus of claim 14 wherein said cooling means provide for a fluid flow at a pressure of more than ten pounds per square inch.

16. The apparatus of claim 1 wherein said vacuum reversal means are functionally effective to bring the vacuum in said chamber surrounding the cryogenic surface to one atmosphere prior to sample delivery, the type and temperature of the gas used for vacuum reversal being independently variable.

17. The apparatus of claim 1 wherein said sample delivery assembly comprises a pneumatically operated plunger mounted in a support structure, said plunger being movable into and out of said chamber, said support structure being cooperatively engaged to said chamber, said plunger being cooperatively aligned with said cryogenic surface such that said plunger's path of travel permits said plunger and the biological tissue mounted thereon to penetrate into said chamber and into a mated position with said cryogenic surface.

18. The apparatus of claim 1 wherein said sample delivery assembly further includes a movable shutter, said shutter controlling access of said plunger into said chamber, the shutter-plunger system being cooperatively timed to allow minimum exposure of the cryogenic surface during sample delivery.

19. The apparatus in claim 1 wherein said sample delivery assembly further includes a sample holder, said sample holder being characterized by a construction which minimizes compression and bounce upon contact with said cryogenic surface.

20. The apparatus of claim 20 wherein said sample holder includes a magnetic disk; a foam rubber cushion; a brass plate; and mounting means for said biological tissue.

21. Apparatus for the vitrification of biological tissue comprising:
(a) a cryogenic surface adapted to receive biological tissue and to ultrarapidly cool said biological tissue, said cryogenic surface being enclosed within a chamber, said cryogenic surface being made from a material selected from the group consisting of: cooper, gold, silver, sapphire, diamond or combinations thereof;
(b) vacuum means functionally attached to said chamber and adapted to reduce the pressure of the atmosphere surrounding said cryogenic surface to from $1 \times 10^{-4}$ mbar to $1 \times 10^{-10}$ mbar;
(c) cooling means functionally associated with said cryogenic surface and said chamber, said cooling means including a source of fluid coolant selected from the group consisting of: helium, liquid nitrogen, propane or combinations thereof;
(d) vacuum reversal means comprising a source of gas, said vacuum reversal means being functionally associated with said chamber to increase the pressure of the atmosphere surrounding said cryogenic surface to atmosphereic;
(e) a sample delivery assembly functionally associated with said cryogenic surface and said chamber, said assembly including means for mounting said biological tissue and means adapted to transfer said biological tissue from outside said chamber to said cryogenic surface inside said chamber; and
(f) a cartridge heater functionally associated with said cryogenic surface said cartridge heater being effective to permit rapid regeneration of said cryogenic surface.

* * * * *